US00PP31238P3

(12) United States Plant Patent
Berry

(10) Patent No.: US PP31,238 P3
(45) Date of Patent: Dec. 17, 2019

(54) ***HIBISCUS* PLANT NAMED 'JBG 14025'**

(50) Latin Name: *Hibiscus rosa-sinensis*
Varietal Denomination: JBG 14025

(71) Applicant: Capstone Plants, Inc., Grand Saline, TX (US)

(72) Inventor: James Berry, Edgewood, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 15/998,306

(22) Filed: Aug. 2, 2018

(65) Prior Publication Data

US 2019/0045691 P1 Feb. 7, 2019

Related U.S. Application Data

(60) Provisional application No. 62/605,169, filed on Aug. 3, 2017.

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 5/02; A01H 6/60; A01H 6/608
See application file for complete search history.

(56) References Cited

PUBLICATIONS

Hollywood *Hibiscus* Gossip Queen 2018, retrieved on May 23, 2019, retrieved from the Internet at https://www.hollywoodhibiscus.com/portfolio/hollywood-hibiscus-gossip-queen-ppaf, 3 pp. (Year: 2018).*

Wright Greenhouse Grower 2017, retrieved on 5/23/19 at www.greenhousegrower.com/varieties/29-new-flowering-and-foliage-plants-fronn-tpie-2017/?e=INSERT_EMAIL&utm_source=realmagnet&utm_medium=newsletter&utm_campaign=ggenews+01252017#Tinsel/134970/20,p. 1 (Year: 2017).*

* cited by examiner

*Primary Examiner* — June Hwu
(74) *Attorney, Agent, or Firm* — The Webb Law Firm

(57) ABSTRACT

A new and distinct *Hibiscus* plant having yellow/orange colored flowers with pink colored tones present that last for several days on the plant over a long flowering season.

1 Drawing Sheet

Botanical classification: *Hibiscus rosa-sinensis.*
Varietal denomination: 'JBG 14025'.

BACKGROUND OF THE INVENTION

The present invention comprises a new and distinct *Hibiscus* plant having the varietal name 'JBG 14025'. The new variety is the result of a planned breeding program with the purposes of developing *Hibiscus rosa-sinensis* plants that exhibit pathogen resistance, multi-day flowers with unique coloration, and possess desirable production traits. 'JBG 14025' is the result of a cross conducted in Grand Saline, Tex. between *Hibiscus rosa-sinensis* varieties 'JBG 12009' (female parent, unpatented) and 'JBG 8413-4' (male parent, unpatented). The new variety was selected in March of 2014 in Grand Saline, Tex. and the first asexual reproduction of the new variety was conducted by semi-mature, softwood cuttings in December of 2014 in Grand Saline, Tex. 'JBG 14025' has been trial and field tested and has been found to retain its distinctive characteristics and remain true to type through successive propagations. The present invention has not been evaluated under all possible environmental conditions. The phenotype may vary with variations in environment without a change in the genotype of the plant.

'JBG 14025' is similar to its female parent in having flowers with overlapping petals with pink colored tones present and a dark throat color, but differs from its female parent in having yellow/orange colored flowers and an increased bud count. 'JBG 14025' is similar to its male parent in having overlapping petals with shades of yellow color present and a dark throat color, but differs from its male parent in having smaller flowers with orange/yellow colored flowers and an increased bud count.

When 'JBG 14025' is compared to *Hibiscus rosa-sinensis* variety 'JBG 14006' (U.S. Plant Pat. No. 30,597), both varieties exhibit overlapping petals. However, the flowers of 'JBG 14025' are yellow/orange in color, while the flowers of 'JBG 14006' are light red in color. Further, the petals of 'JBG 14006' are more ruffled in appearance than 'JBG 14025'.

The following traits distinguish 'JBG 14025' as a new and distinct cultivar from other *Hibiscus* varieties known to the breeder:

1. Yellow/orange colored flowers with pink colored tones present;
2. Overlapping flower petals;
3. Resistance to bacterial leaf spot (*Pseudomonas* spp.); and
4. Multi-day flowers.

DESCRIPTION OF THE DRAWING

The accompanying photographic image illustrates the new variety at approximately one year of age, with the colors being as nearly true as is possible with color illustrations of this type:

FIG. 1 illustrates a close-up view of a flower of the new variety.

DESCRIPTION OF THE PLANT

The following detailed description sets forth the characteristics of the new variety. The color readings and measurements were taken in the summer in Grand Saline, Tex. under natural light on approximately one year old, growing plants in 24.0 cm diameter containers. Color references are primarily to The 1995 R.H.S. Colour Chart of The Royal Horticultural Society of London, 3rd Edition, except where general color terms are used.

PLANT

Time to initiate roots: About 47 days at an average of 24° C.
Time to develop roots: About 52 days at an average of 24° C.
Time to produce a finished flowering plant from a rooted cutting: About 30 weeks in a 24.0 cm diameter container.
Specific disease/pest resistance: Resistance to bacterial leaf spot (*Pseudomonas* spp.).
Heat/cold tolerance: Nothing unusual noted to date; not hardy below 33° F.
Drought tolerance: Nothing unusual noted to date.
Plant:
- *Type*.—Tropical, ornamental shrub.
- *Habit*.—Upright.
- *Height*.—120.0 cm at maturity.
- *Spread*.—90.0 cm at maturity.
- *Vigor*.—Medium.

Rooting vigor: Strong.
Stem:
- *Number per plant*.—9.
- *Length*.—Ranging from 30.0-60.0 cm.
- *Width*.—1.0-2.5 cm.
- *Texture*.—Immature: Smooth. Mature: Vertically ridged.
- *Strength*.—Moderate.
- *Branch number*.—Moderate; 9.
- *Internode length*.—1.5-2.5 cm.
- *Color*.—Immature: 145B. Mature: 199B.
- *Stipules*.—Number per node: 2. Shape: Lanceolate. Length: 1.0 cm. Width: 1.0 mm. Surface texture: Smooth. Apex: Attenuate. Base: Linear. Margin: Entire. Color: 145B.

Foliage:
- *Arrangement*.—Alternate; simple.
- *Size of leaf*.—Length: 7.0 cm. Width: 5.5 cm.
- *Shape of leaf* (*generally*).—Ovate.
- *Shape of apex*.—Acute.
- *Shape of base*.—Rounded.
- *Texture* (*both surfaces*).—Smooth.
- *Margin type*.—Slightly crenate.
- *Color*.—Young leaves: Upper surface: 137A. Lower surface: 137C. Mature leaves: Upper surface: 137A. Lower surface: 137C.
- *Veins*.—Venation type: Pinnate. Color: Upper surface: 138B. Lower surface: 138B.
- *Petiole*.—Length: 2.5-3.0 cm. Diameter: 3.0 mm Texture: Smooth. Color: 141C.

FLOWERS

Buds (described at immaturity):
- *Shape*.—Lanceolate.
- *Diameter*.—2.0 cm.
- *Length*.—2.5 cm.
- *Color*.—145A.

Natural flowering season: From spring through fall in Grand Saline, Tex.
Flower type and habit: Single, with overlapping petals.
Fragrance: None observed.
Flowers (described on the first day of full opening):
- *Number per stem*.—1.
- *Overall depth*.—8.0 cm.
- *Overall diameter*.—14.0 cm.
- *Shape*.—Rotate; regular.
- *Lastingness*.—3 days on the plant.
- *Petals*.—Number: 5. Arrangement: Simple. Length: 7.0 cm. Width: Apex: 5.5 cm. Base: 2.0 cm. Shape: Obovate. Apex: Obtuse. Base: Cuneate. Margin: Slightly ruffled. Incisions: Absent. Texture/appearance: Upper surface: Velvety. Lower surface: Smooth. Color (when opening and fully opened): Upper surface: Throat: 53B to 54A at 4.0-5.0 cm. Eye: No clearly defined eye present because of a bleeding throat color. Eye zone extension: 54A to 56A to 56D — short in length (2.0-3.0 cm arising from throat). Petal: 24B at edge of throat to 15B at apex. Lower surface: 15A at the apex through the center to 48A at the base.
- *Calyx*.—Form: Fused. Overall length: 3.0 cm. Overall diameter: 1.5-3.5 cm. Sepals/calyx lobes: Number: 7. Shape: Acute. Apex: Acuminate. Margin: Entire. Texture: Smooth. Color: Outer surface: 137B. Inner surface: 137B.
- *Epicalyx*.—Length: 1.5 cm. Width: 5.0 mm. Texture: Smooth. Color: 147B.
- *Bracts*.—Not present.
- *Peduncle*.—Length: 3.5 cm. Diameter: 0.5 mm. Strength: Strong. Angle: 45°. Texture: Smooth. Color: 144B.

Reproductive organs:
- *Gynoecium*.—Pistils: Number: 1. Length: 7.5 cm. Stigma: Number: 5. Shape: Round. Length: 5.0 mm. Diameter: 3.0 mm. Color: 33A. Style: Length: 6.5 cm. Width: 5.0 mm. Color: 10D at the apex to 52B at the base. Ovary: Shape: Attenuate. Length: 1.25 cm. Width: 1.0 cm. Color: 52B.
- *Androecium*.—Stamens: Number: 79. Position: Just below the stigma on the style. Anther: Shape: U-shaped. Diameter: 2.0 mm. Color: 19A. Filament: Length: 5.0 mm. Width: 1.0 mm. Color: 10D. Pollen: Color: 19A. Amount (generally): Moderate.

SEEDS

Seeds:
- *Number*.—From 0 to 20.
- *Color*.—200C.
- *Length*.—5.0 mm.
- *Width*.—5.0 mm.

I claim:

1. A new and distinct variety of *Hibiscus* plant, as is herein illustrated and described.

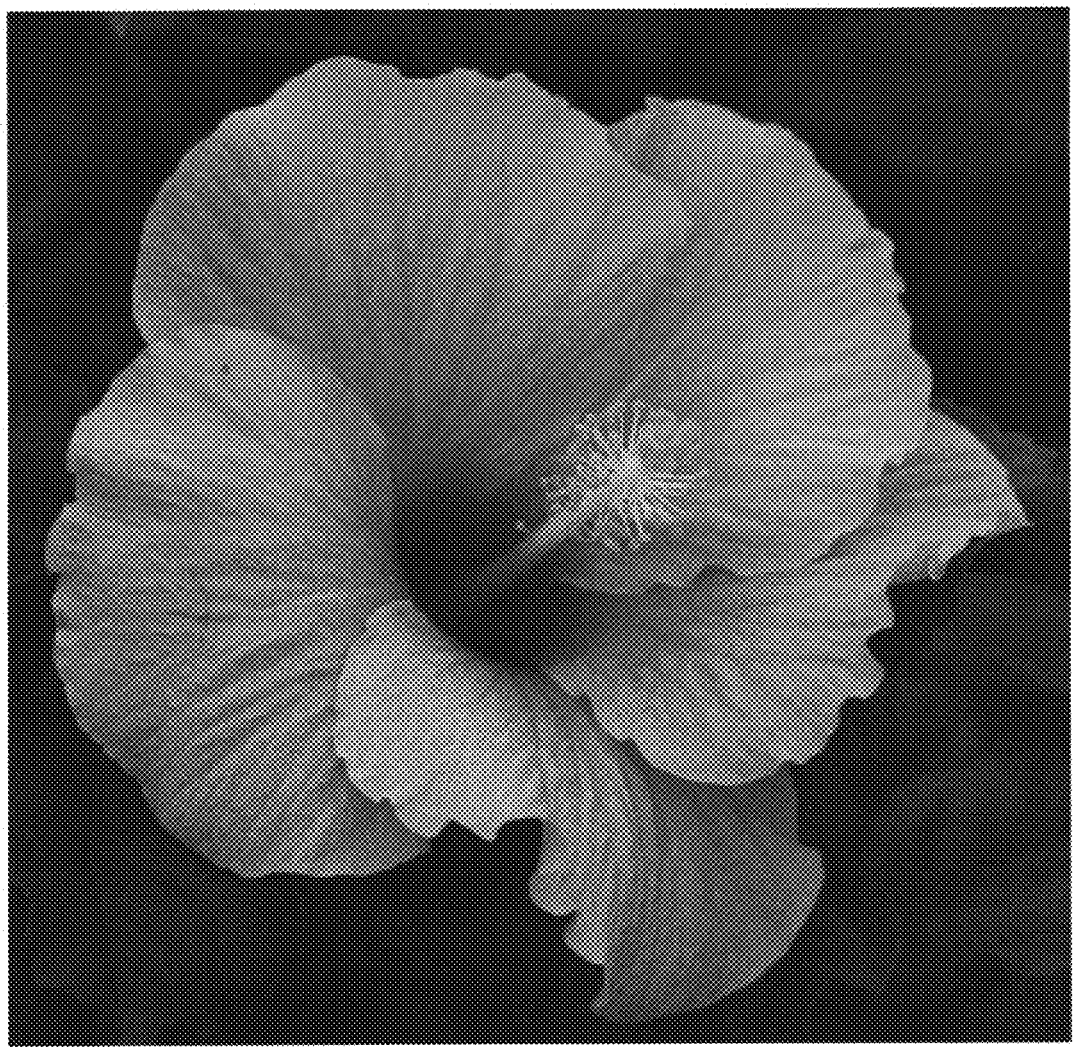

* * * * *